United States Patent [19]

Hagemeyer et al.

[11] Patent Number: 5,691,262
[45] Date of Patent: Nov. 25, 1997

[54] REGENERATION OF CATALYSTS USED IN OXIDATIVE DEHYDROGENATION OF ALKYLAROMATICS AND PARAFFINS

[75] Inventors: Alfred Hagemeyer; Otto Watzenberger, both of Ludwigshafen; Axel Deimling, Neustadt, all of Germany

[73] Assignee: BASF Aktiengesellschaft, Ludwigshafen, Germany

[21] Appl. No.: 542,185

[22] Filed: Oct. 12, 1995

[30] Foreign Application Priority Data

Oct. 18, 1994 [DE] Germany .......................... 44 37 252.3

[51] Int. Cl.$^6$ .............................. B01J 38/12; B01J 38/32
[52] U.S. Cl. .................................... 502/38; 502/44
[58] Field of Search ................... 502/38, 41, 44

[56] References Cited

U.S. PATENT DOCUMENTS 3,118,007  1/1964  Kronig et al. ........................ 260/680

FOREIGN PATENT DOCUMENTS

| 397 637 | 11/1990 | European Pat. Off. | ........ C07C 15/40 |
| 403 462 | 12/1990 | European Pat. Off. | .......... C07C 5/32 |
| 482 276 | 4/1992 | European Pat. Off. | ........ C07C 15/40 |
| 885 422 | 12/1961 | United Kingdom . | |

*Primary Examiner*—Glenn A. Caldarola
*Assistant Examiner*—Alexander G. Ghyka
*Attorney, Agent, or Firm*—Keil & Weinkauf

[57] ABSTRACT

A regenerative process for the preparation of olefinically unsaturated compounds by oxidation/dehydrogenation of selectively oxidizable hydrocarbons over an oxygen carrier acting as catalyst, in the absence of molecular oxygen, alternating (in repeated cycles) with regeneration of the spent oxygen carrier with a gaseous molecular oxidizing agent, in which the spent (reduced) catalyst is cooled, prior to introduction of the regenerating gas, to a temperature which is below the temperature of the reaction, regeneration being controlled in such a manner that the highest temperature occurring during regeneration does not exceed the temperature of reaction at which dehydrogenation is commenced.

6 Claims, No Drawings

REGENERATION OF CATALYSTS USED IN OXIDATIVE DEHYDROGENATION OF ALKYLAROMATICS AND PARAFFINS

The invention relates to a process for the preparation of olefinically unsaturated compounds by catalytic oxidation, i.e. oxidative dehydrogenation, by transferring oxygen from a previously oxidized oxygen carrier acting as catalyst in the absence of molecular oxygen. The invention preferably relates to the catalytic oxidative dehydrogenation of alkylaromatics and paraffins to form the corresponding alkenyl aromatic compounds and olefins, in particular the dehydrogenation of ethyl benzene to styrene with the formation of water.

Styrene and divinyl benzene are important monomers for industrial plastics and are used in large quantities.

Styrene is prepared over modified iron oxide catalysts mainly by non-oxidative dehydrogenation of ethyl benzene, one mole of hydrogen being formed per mole of styrene. Unfortunately this reaction is an equilibrium reaction which takes place at temperatures typically of from 600° to 700° C. and proceeds at a conversion of ca 60% and a styrene selectivity of approximately 90%, the reverse reaction commencing with increasing conversion and increasing concentration of the target product, which factor thus restricts the final degree of conversion.

By contrast, the use of oxidative dehydrogenation, in which the hydrocarbon to be converted is caused to react with molecular oxygen, i.e. generally air, produces almost quantitative conversion, since in this case water is formed. In addition this reaction takes place at a lower temperature than the non-oxidative dehydrogenation. A drawback of the oxidative dehydrogenation using molecular oxygen is that total oxidation takes place as a side reaction, with the result that carbon dioxide and further amounts of water occur in the product stream. This phenomenon is frequently referred to as "gasification".

It has therefore been proposed to use an oxygen carrier consisting of a reducible metal oxide which acts as catalyst, i.e. has an influence on the reaction, instead of molecular oxygen. The oxygen carrier undergoes continuous exhaustion and has to be regenerated in a second step to restore the initial activity. This method is frequently used in classical process engineering and is known as the regenerative technique. In the reactivation phase any coke deposits, for example, can also be calcined. The regeneration process is highly exothermal, so that the liberated waste heat can be utilized for the production of steam, for example. By decoupling the reduction and oxidation steps the selectivity can be significantly increased.

From an engineering point of view there are two ways of effecting decoupling, i.e. spatial and temporal separation of the two partial steps.

When effecting spatial separation of the two partial steps a moving bed is used, the catalyst particles being conveyed from the dehydrogenation zone to a separate regenerating reactor, following separation of the reaction products, in which regenerating reactor reoxidation takes place. The regenerated catalyst is recycled to the dehydrogenation zone. Such a process can be set up for continuous, i.e. cyclical operation. The catalyst is exposed to high mechanical stresses and must therefore possess adequate hardness.

Temporal separation can be realized when using a fixed bed oxygen carrier by switching periodically between the useful reaction and the regeneration, optionally following a purging phase using inert gas.

The principle of regeneration using a reducible and reactivatable catalyst was first described for the oxidation or ammonoxidation of propene to produce acrolein and acrylic acid or acrylonitrile respectively (GB 885,422; GB 999,629; K. Aykan, J. Catal. 12 (1968) 281–190), arsenate and molybdate catalysts being used. The use of the regenerative method in the oxidative dehydrogenation of aliphatic alkanes to produce mono- and di-olefins using ferrite catalysts (e.g., U.S. Pat. No. 3,440,299 DE 2,118,344, DE 1,793,499) is likewise known, as is also the use thereof for the oxidative coupling of methane to form higher hydrocarbons; catalysts of various structures are used in this process (e.g. U.S. Pat. No. 4,795,849, DE 3,586,769 using Mn/Mg/Si oxides; U.S. Pat. No. 4,568,789 using Ru oxide; EP 254,423 using Mn/B oxides on MgO; GB 2,156,842 using $Mn_3O_4$ spinels). Also the dehydrodimerisation of toluene to produce stilbene in the absence of free oxygen by means of reducible catalysts such as Bi/In/Ag oxides is known (EP 30.837). Finally the principle is still employed for the dehydrogenation, dehydrocyclisation, and dehydroaromatisation of paraffins for the improvement of gasoline (U.S. Pat. No. 4,396,537 using Co/P-oxide catalysts).

EP 39,737 and 403,462 disclose that it is possible to use this type of process for the oxidative dehydrogenation of paraffins and alkylaromatics. According to said references reducible metal oxides are used, selected from the group consisting of V, Cr, Mn, Fe, Co, Pb, Bi, Mo, U, and Sn, applied to supports composed of clays, zeolites and oxides of Ti, Zr, Zn, Th, Mg, Ca, Ba, Si, Al.

Although a high yield is reportedly obtained with these catalysts, very intense gasification (total combustion) occurs in the initial phase of the dehydrogenation, when the hydrocarbon comes into contact with the freshly regenerated and therefore particularly active catalyst. Apart from the loss of raw materials there is the further consideration that considerably more oxygen is consumed than for the mere dehydrogenation, so that the oxygen carrier becomes prematurely exhausted and the cycle period is shortened unnecessarily.

Thus, when this reaction concept is to be utilized industrially, it is particularly important to suppress the initial total oxidation as far as possible.

EP 482,276 has therefore proposed the partial prereduction of the freshly regenerated catalyst, for example using $H_2$ or CO, before the catalyst is brought into contact with the starting hydrocarbon in the dehydrogenation zone. This measure does indeed improve the initial selectivity, but the process requires an additional step and the use of an expensive reducing agent which is foreign to the reaction. The problem of initial gasification apparently also exists in other oxidation reactions carried out industrially using redox systems, for the partial prereduction of the catalyst as remedial action has also been proposed elsewhere (cf. JA 127,819).

It is the object of the present invention to provide a process which reduces the gasification in the initial phase of the dehydrogenation, increases the selectivity toward the desired product, and can do without elaborate additional process engineering steps such as partial prereduction using an expensive reducing agent such as $H_2$, CO, etc.

We have now found that the regeneration of a conventional redox catalyst (oxygen carrier) to form a fresh catalyst produces a distinctly reduced tendency to initial gasification and thus an improvement of the initial selectivity when the following procedure is adopted:

1. The spent (reduced) catalyst is cooled, prior to reoxidation, i.e. prior to the introduction of the regenerative stream either still in the presence of the reaction mixture having a reducing action, i.e. in the presence of the educt itself, or, preferably, under a blanket of inert gas (which can be the same as the purging gas), to a temperature $T_{reg}$, which is below the temperature of the reaction $T_{react}$. Preferably the difference between $T_{reg}$ and $T_{react}$ is from 20 to 100K.

2. Regeneration is started at said (lower) temperature $T_{reg}$ by the introduction of the oxidizing agents, i.e., in particular oxygen, air, impoverished air, or $N_2O$, regeneration being controlled in such a manner that the highest temperature occurring during regeneration, the so-called hot-spot temperature, does not exceed the temperature of reaction $T_{react,0}$ at which oxidation/dehydrogenation is commenced.

Following the removal of the oxidizing environment, i.e. in the absence of the oxidizing agents, preferably under a blanket of inert gas, which may again, if desired, be identical to the purging gas, the regenerated catalyst is heated to the (initial) reaction temperature $T_{react,0}$ and only then is the reaction started by the introduction of the hydrocarbon (educt).

Thus, during the latter heating step (3) no reducing agent should be present, since this would immediate react with the fresh catalyst and thus itself be consumed whilst subjecting the catalyst to useless pre-reduction and unnecessarily consuming its oxygen load, as occurs, for example, in the method of partial pre-reduction described in EP 482,276 and JP 127,819.

The following is a detailed description of the individual steps of the invention. Since the regeneration is exothermal, the temperature of the catalyst will rise and would reach local peak values (hot-spots) after a time if measures were not taken to ensure that the initial regeneration phase is sufficiently attenuated.

The important feature of the invention is that the peak temperature (hot-spot) attained during regeneration is lower than the starting temperature used for the actual reaction, since this reaction step is also associated with enthalpy effects, that is to say, the temperature of the catalyst will change during said actual reaction. (Since the invention relates only to initial gasification, it is only necessary to compare the temperature of the catalyst with said initial reaction temperature). Thus, in the case of adiabatic regeneration, the spent catalyst must be cooled to a lower value than that calculated for adiabatic temperature increase from the formation enthalpy. For example a catalyst consisting of bismuth on a titanium oxide support (as described in a non pre-published proposal) gives a calculated value of from approximately 50 to 100K, depending on the loading (i.e. the reaction pressure for example), the degree of reduction (exhaustion) of the spent catalyst after employment in the dehydrogenation, and the oxygen concentration in the regenerating gas. Cooling to a further extent has an additional preventive effect as regards the occurrence of hot-spots.

As to the reason for the success of the process of the invention we offer the following postulate (to which the invention is not to be restricted): (molecular) oxygen chemisorbed on the surface of the catalyst and responsible for the total oxidation of the educts is converted by the measures of the invention to less reactive and therefore more selective grid oxygen, since the oxygen uptake of the redox catalyst is greater at higher temperatures. Thus the process of the invention could be called a process for the removal of chemisorbed oxygen from the surface of redox-active metal oxides.

Our method of reducing the initial gasification and improving the initial selectivity toward the desired product is described below by way of example with reference to the unsteady oxidative dehydrogenation of ethylbenzene but is equally well applicable to other oxidizing reactions.

Suitable catalysts for use in the above process are theoretically all catalysts containing reducible metal oxides such as oxides of Bi, V, (De, Fe, In, Ag, Cu, Co, Mn, Pb, Sn, Mo, W, As, Sb, preferably Bi oxide, Ce oxide, and V oxide, and more preferably $Bi_2O_3$ or $CeO_2$ and which can be used as supported or unsupported catalysts. The supports used are preferably oxides of transition metals such as titanium oxide or chromium oxide, preferably $TiO_2$ and $Cr_2O_3$.

A suitable catalyst contains or consists of, for example, from 5 to 60 wt %, preferably from 10 to 45 wt % of vanadium, from 10 to 95 wt %, preferably from 30 to 80 wt % of chromium or titanium and from 1 to 40%, preferably from 3 to 20 wt % of alkali metal and/or alkaline earth metal and/or a rare earth (always determined in terms of the most stable oxide) and contains, when chromium oxide is used as support, from 0 to 70 wt %, preferably from 10 to 50 wt %, of a catalytically ineffective oxide i.e. an inorganic binding agent, preferably an aluminum oxide. The above proportions also apply to the aforementioned other elements which can be used instead of vanadium.

Another favorable catalyst contains or consists of from 5 to 60 wt %, preferably from 10 to 45 wt % of cerium(IV) oxide on a support consisting of from 10 to 95 wt %, preferably from 20 to 80 wt %, of chromium(III) oxide with from 1 to 40 wt %, preferably from 3 to 20 wt %, of alkali metal and/or alkaline earth metal (determined as oxide) and contains from 0 to 70 wt %, preferably from 10 to 60 wt %, of aluminum oxide.

A particularly preferred catalyst contains or consists of from 5 to 60 wt %, preferably from 10 to 45 wt %, of bismuth(III) oxide on a support consisting of from 10 to 95 wt %, preferably from 30 to 80 wt %, of chromium(III) oxide and/or titanium oxide together with from 1 to 40 wt %, preferably from 3 to 20 wt %, of alkali metal and/or alkaline earth metal and contains from 0 to 70 wt %, preferably from 10 to 60 wt % of aluminum oxide.

The above proportions relate to the finished catalyst in its most stable oxidation stage or in the oxidation stage stated. Thus the above is not intended to imply statements on the actual bonding ratios, to which the invention is not restricted; for example, during calcination other phases can form which correspond to higher oxidation stages but are not actually oxides, such as chromates or bichromates of potassium or bismuth.

The catalyst can be prepared in the usual manner such as by dry mixing, slurrying, impregnation, precipitation, spray drying, etc. The ingredients can be used, e.g., in the form of their oxides, hydroxides, carbonates, acetates, nitrates or generally water-soluble salts with organic or inorganic anions, which convert on heating (calcination) to the corresponding oxides. Transition metal complexes can also be used, for example. Calcination is carried out at temperatures in the range of from 200° to 1000° C., preferably from 200° to 800° C. and in particular from 400° to 700° C.

The regeneration or reactivation of the catalyst is carried out at temperatures in the range of from 100° to 600° C., preferably from 250° to 500° C. using a molecular oxidizing agent. Examples of suitable agents are air, impoverished air, oxygen, and $N_2O$. A diluent can also be used. Regeneration can be carried out under reduced pressure or under atmospheric or superatmospheric pressure. Pressures are preferred in the range of from 500 mbar to 10 bar.

The dehydrogenating reaction requires a temperature of from 200° to 800° C., preferably from 350° to 550° C. at atmospheric pressure or a slightly reduced or elevated pressure, e.g. a pressure of from 100 mbar to 10 bar, preferably from 500 mbar to 2 bar, at a liquid hourly space velocity (LHSV) of from 0.01 to 20 $h^{-1}$ and preferably from 0.1 to 5 $h^{-1}$. In addition to the hydrocarbon to be hydrogenated, diluents such as $CO_2$, $N_2$, nobel gases, or steam may be present.

The process of the invention is demonstated below by way of example with reference to the unsteady oxidative dehydrogenation of ethyl benzene to form styrene, but is equally well applicable to other oxidizing reactions.

The catalytic oxidative dehydrogenation of ethyl benzene to produce styrene is carried out in a pulsating reactor at reaction temperatures in a range of 450°–550° C. In this process a fixed micro bed is acted upon (initial weight of catalyst: 0.3–0.6 g) pulsation being caused by pure ethyl benzene in the total absence of free oxygen, and the resulting reaction products are examined by quantitative gas-chromatographic analysis for each pulse. Helium flows as carrier gas through the reactor between two successive ethyl benzene pulses (ca 1.5 min). An individual pulse contains 380° mg of ethyl benzene. The rate of flow of the carrier gas is 21.5 ml/min. In this way deactivation of the catalyst could be monitored at a high time resolution and without the occurrence of dead times right from the start.

At the commencement of the reaction the catalyst is highly active so that high conversions of ethylbenzene are observed. Due to an increased formation of by-products (e.g., gasification to carbon oxides) the high initial activity often leads to losses of selectivity toward styrene. As the reaction proceeds, the formation of by-products declines and the selectivity toward styrene then improves constantly up to a final value typical of the catalyst under consideration. As the time of the experiment increases the catalyst is progressively deactivated at the rate at which its grid oxygen is consumed, so that the ethyl benzene conversion sinks. Regeneration is carried out after 90 pulses. The results show that the yield of styrene, in terms of the product of selectivity and conversion, generally passes through a flat peak.

On completion of the dehydrogenation reaction the regeneration of the spent, i.e. reduced, catalyst is carried out as proposed for the process of the invention. A new dehydrogenation cycle follows using the reactivated catalyst. Several cycles are run.

For all catalysts under consideration the catalytic activity could be restored to its full extent by reoxidation of the deactivated, reduced catalysts. No loss of activity increasing with on-stream time could be found. The figures given in Table 1are averages taken over a number of experiments.

COMPARATIVE EXAMPLE 1

A redox catalyst consisting of 12.5% of $K_2O$, 15% of $La_2O_3$, 25% of $Bi_2O_3$, remainder $TiO_2$ was placed in a fixed micro bed in a pulsating reactor (catalyst capacity approx. 1 ml, 90 pulses per cycle, regeneration with air for a period of 45 min) and was used for a number of experiments carried out at reaction temperatures of 490° C., 500° C., and 510° C. respectively. The conversion, selectivity, and yield attained in the oxidative dehydrogenation of ethylbenzene to styrene were determined.

In each case, the temperature used for regeneration was the same as that used for the reaction.

EXAMPLE 1

The same reaction temperatures were used as in Comparative Example 1 (i.e. 490° C., 500° C., and 510° C.), but regeneration was carried out at lower temperatures than the dehydrogenation. On completion of the reaction (90th pulse) the reactor was cooled under a blanket of helium to 380° C., 400° C., and 400° C. respectively and the regeneration was then started (45 min using air, gas flow rate ca 25 ml/min), followed by a switch from air to helium (gas flow rate ca 21 ml/min of He) and reheating under a blanket of helium to the initial reaction temperatures of 490° C., 500° C., and 510° C. respectively, after which dehydrogenation was started as described in Comparative Example 1.

COMPARATIVE EXAMPLE 2

A redox catalyst consisting of 15% of $K_2O$, 15% of $La_2O_3$, 25% of $Bi_2O_3$, remainder $TiO_2$ was placed in a fixed micro bed in a pulsating reactor (catalyst capacity approx. 1 ml, 90 pulses per cycle, regeneration with air for a period of 45 min) and was used for an experiment carried out at a reaction temperature of 500° C. Conversion, selectivity, and yield attained in the oxidative dehydrogenation of ethylbenzene to styrene were determined.

The temperature used for regeneration was the same as that used for the reaction, i.e. 500° C.

EXAMPLE 2

Comparative Example 2 was repeated except that regeneration was carried out at a lower temperature than the dehydrogenation. On completion of the reaction (90th pulse) the reactor was cooled under a blanket of helium to 420 ° C. and the regeneration was then started (45 min using air, gas flow rate ca 25 ml/min), followed by a switch from air to helium (gas flow rate ca 21 ml/min of He) and reheating under a blanket of helium to the reaction temperature of 500° C., after which dehydrogenation was started as described in Comparative Example 2.

COMPARATIVE EXAMPLE 3

A redox catalyst consisting of 12.5% of $K_2O$, 15% of $La_2O_3$, 25% of $Bi_2O_3$, remainder $TiO_2$ was placed in a fixed micro bed in a pulsating reactor (catalyst capacity approx. 1 ml, 90 pulses per cycle, regeneration with air for a period of 45 min) and was used for an experiment carried out at a reaction temperature of 500° C. Conversion, selectivity, and yield attained in the oxidative dehydrogenation of ethylbenzene to styrene were determined.

The temperature used for regeneration was lower than that used for the reaction, as in the process of the invention, but the catalyst was kept under air instead of inert gas during the period of reheating to reaction temperature following reactivation of the catalyst. The procedure was as follows:

On completion of the reaction (90th pulse) the reactor was cooled under a blanket of helium to 400° C. and regeneration was then started (45 min using air, gas flow rate ca 25 ml/min), after which the stream of air was not cut off and reheating to the reaction temperature of 500° C. took place under air. Dehydrogenation was then started as described in Comparative Example 1.

TABLE 1

| Initial Gasification and Styrene Yield in the first pulse | | | |
|---|---|---|---|
| Comparative Experiment 1 | | Example 1 | |
| $T_{reg}*$ | $T_{react}*$ | $T_{reg}*$ | $T_{react}*$ |
| 490° C. | 490° C. | 380° C. | 490° C. |

TABLE 1-continued

Initial Gasification and Styrene Yield in the first pulse

| | | | | | | |
|---|---|---|---|---|---|---|
| Gas | 22.5% | | Gas | 11.1 % | | |
| Styrene | 69.2% | | Styrene | 79.5 % | | |
| 500° C. | | 500° C. | 400° C. | | 500° C. | |
| Gas | 27.8% | | Gas | 17.4% | | |
| Styrene | 60.1% | | Styrene | 68.8% | | |
| 510° C. | | 510° C. | 400° C. | | 510° C. | |
| Gas | 31.1% | | Gas | 20.9% | | |
| Styrene | 54.2% | | Styrene | 63.3 % | | |

| Comparative Experiment 2 | | | | Example 2 | | |
|---|---|---|---|---|---|---|
| 500° C. | | 500° C. | 420° C. | | 500° C. | |
| Gas | 21.2% | | Gas | 10.6% | | |
| Styrene | 69.2% | | Styrene | 77.7% | | |

Comparative Experiment 3
Temp. Jump Regeneration
(Reheating after reactivation
in air instead of in He)

| $T_{reg}$* | | $T_{react}$* | |
|---|---|---|---|
| 400° C. | | 500° C. | |
| Gas | 22.1% | | |
| Styrene | 66.2% | | |

*$T_{reg}$ = temperature of regeneration
*$T_{react}$ = temperature of reaction

Table 1 gives a summary of the results. It gives the data for the initial gasification and the yield of styrene in the first pulse, i.e. at the very start of the reaction, when total oxidation is at its highest level. In the 4th and 7th pulses (which are routinely measured) there is also a slight reduction in the amount of gas present and a corresponding increase in the yield of styrene of about 1%.

We claim:

1. A regenerative process for the preparation of olefinically unsaturated compounds by oxidation of selectively oxidizable hydrocarbons at a temperature $T_{react}$ over oxygen carrier acting as catalyst, in the absence of molecular oxygen, alternating (in repeated cycles) with regeneration of the spent oxygen carrier with a gaseous molecular oxidizing agent, characterized by the following steps:

the spent (reduced) catalyst is cooled, prior to the introduction of the regenerative gas either still in the presence of the reaction mixture having a reducing action, or under a blanket of inert gas, to a temperature $T_{reg}$, which is below the temperature of the reaction $T_{react}$;

regeneration is started at temperature $T_{reg}$ by the introduction of the oxidizing agents, regeneration being controlled in such a manner that the highest temperature occurring during regeneration does not exceed the temperature of reaction $T_{react,0}$ at which oxidation/dehydrogenation is commenced; and following the removal of the oxidizing environment, the regenerated catalyst is heated to the initial reaction temperature $T_{react,0}$ and only then is the hydrocarbon (educt) to be oxidized introduced.

2. A process as defined in claim 1, wherein alkylaromatics and parafins are subjected to catalytic oxidative dehydrogenation to produce the corresponding alkenylaromatic compounds and olefins.

3. A process as defined in claim 1, wherein ethylbenzene is subjected to catalytic oxidative dehydrogenation to produce styrene.

4. A process as defined in claim 1, wherein the difference between $T_{react}$ and $T_{reg}$ is from 20 to 100K.

5. A process as defined in claim 1, wherein a catalyst is used which contains at least one reducible metal oxide selected from the group consisting of the oxides of Bi, V, Ce, Fe, In, Ag, Cu, Co, Mn, Pb, Sn, Mo, W, As, and/or Sb, supported or unsupported.

6. A process as defined in claim 5, wherein the support used for the catalyst is an oxide of a transition metal such as titanium oxide or chromium oxide.

* * * * *

UNITED STATES PATENT AND TRADEMARK OFFICE
CERTIFICATE OF CORRECTION

PATENT NO.: 5,691,262

DATED: November 25, 1997

INVENTOR(S): HAGEMEYER et al.

It is certified that error appears in the above-identified patent and that said Letters Patent is hereby corrected as shown below:

Column 8, claim 2, line 2, "parafins" should be --paraffins--.

Signed and Sealed this

Thirty-first Day of March, 1998

*Attest:*

BRUCE LEHMAN

*Attesting Officer*     *Commissioner of Patents and Trademarks*